United States Patent
Kariyazaki et al.

(10) Patent No.: US 8,180,488 B2
(45) Date of Patent: May 15, 2012

(54) ROBOT SYSTEM

(75) Inventors: Hirokazu Kariyazaki, Fukuoka (JP);
Shinichi Maehara, Fukuoka (JP);
Minoru Yamamoto, Fukuoka (JP);
Michiharu Tanaka, Fukuoka (JP)

(73) Assignee: Kabushiki Kaisha Yaskawa Denki, Fukuoka (JP)

( * ) Notice: Subject to any disclaimer, the term of this patent is extended or adjusted under 35 U.S.C. 154(b) by 240 days.

(21) Appl. No.: 12/793,646

(22) Filed: Jun. 3, 2010

(65) Prior Publication Data

US 2010/0292843 A1 Nov. 18, 2010

Related U.S. Application Data

(63) Continuation of application No. PCT/JP2008/070770, filed on Nov. 14, 2008.

(30) Foreign Application Priority Data

Dec. 7, 2007 (JP) ................ P.2007-316501

(51) Int. Cl.
*G06F 19/00* (2006.01)
(52) U.S. Cl. .................. 700/264; 318/568.17
(58) Field of Classification Search .......... 700/264, 700/245, 95, 248; 901/1, 2, 9, 14, 16, 17, 901/28–30, 42; 318/566, 568.1, 568.11, 318/568.12, 568.15–568.18, 568.2, 568.21, 318/568.23; 706/45–51
See application file for complete search history.

(56) References Cited

U.S. PATENT DOCUMENTS

| 4,482,968 | A * | 11/1984 | Inaba et al. | 318/568.22 |
| 6,212,444 | B1 * | 4/2001 | Kato et al. | 700/255 |
| 7,765,031 | B2 * | 7/2010 | Nagamatsu | 700/255 |
| 2003/0225479 | A1 | 12/2003 | Waled | |
| 2004/0249508 | A1 | 12/2004 | Suita et al. | |
| 2005/0090930 | A1 | 4/2005 | Otsuki et al. | |
| 2006/0052901 | A1 | 3/2006 | Nihei et al. | |

(Continued)

FOREIGN PATENT DOCUMENTS

CN 1609740 4/2005

(Continued)

OTHER PUBLICATIONS

Chinese Office Action for corresponding CN Application No. 200880119409.8, Oct. 19, 2011.

(Continued)

*Primary Examiner* — Dalena Tran
(74) *Attorney, Agent, or Firm* — Ditthavong Mori & Steiner, P.C.

(57) ABSTRACT

A robot system includes a robot and a robot controller including a drive unit, a memory that stores an arm-occupied region and a movement-forbidden region, a target position calculation unit that outputs a target position of a tool or a workpiece, a movement-forbidden region entry monitoring unit that checks whether the arm-occupied region based on the target position enters the movement-forbidden region and outputs a stop request if it is checked that the arm-occupied region enters the movement-forbidden region, and a predicted-coasting-position calculating unit that calculates a predicted coasting position of each axis and a coasting position of the tool or the workpiece in the case that the robot is urgently stopped. The movement-forbidden region entry monitoring unit checks whether the arm-occupied region at the coasting position enters the movement-forbidden region and outputs another stop request if it is checked that the arm-occupied region enters the movement-forbidden region.

5 Claims, 7 Drawing Sheets

U.S. PATENT DOCUMENTS

2007/0118249 A1 5/2007 Nagamatsu

FOREIGN PATENT DOCUMENTS

| CN | 1743148 | 3/2006 |
|---|---|---|
| EP | 1632318 | 3/2006 |
| JP | 62-103769 | 5/1987 |
| JP | 63-041910 | 2/1988 |
| JP | 06-341910 | 12/1994 |
| JP | 07-314378 | 12/1995 |
| JP | 2000-190262 | 7/2000 |
| JP | 2000-315103 | 11/2000 |
| JP | 2002-331478 | 11/2002 |
| JP | 2003-131713 | 5/2003 |
| JP | 2004-322244 | 11/2004 |
| JP | 2005-128686 | 5/2005 |
| JP | 2006-068857 | 3/2006 |
| JP | 2007-144524 | 6/2007 |

OTHER PUBLICATIONS

International Search Report for International Application No. PCT/JP2008/070770, Jan. 27, 2009.

Written Opinion of the International Searching Authority for International Application No. PCT/JP2008/070770, Jan. 27, 2009.

Supplementary European Search Report for corresponding EP Application No. 08858016.2-1239, Oct. 25, 2011.

\* cited by examiner

ROBOT SYSTEM

CROSS-REFERENCE TO RELATED APPLICATIONS

The present application is a continuation application of PCT/JP2008/70770, filed Nov. 14, 2008, which claims priority to Japanese Patent Application No. 2007-316501, filed Dec. 7, 2007. The contents of these applications are incorporated herein by reference in their entirety.

BACKGROUND OF THE INVENTION

1. Field of the Invention

The present invention relates to a robot system that includes an apparatus for limiting movement of a robot.

2. Discussion of the Background

Robots, in particular, industrial robots are widely used, for example, in automobile assembly factories and the like.

When such a robot moves, an operation program (in which a set of instructions for making the robot perform an operation is described), which has been recorded in a memory of a controller, controls movement of a robot arm and a wrist (and a workpiece and a tool attached to the wrist) so as to move the robot arm and the wrist along a desired movement path so that they do not interfere with peripheral equipment and they do not make an unnecessary movement.

A safety barrier is usually disposed so as to surround the movement path of the robot with a predetermined margin so that an accident in which an operator is endangered by the movement of the robot arm and the wrist can be avoided.

The safety barrier is disposed outside the maximum movement range of the robot. For a robot having a small movement range, such as a robot for transporting small components, disposing a safety barrier outside the maximum movement range of the robot increases the space occupied by the robot and results in a waste of space. Therefore, there are existing techniques for limiting the movement range of a robot by using computer control.

For example, JP Patent Publication No. 2004-322244A describes a method for limiting movement of a robot. The method includes defining in a memory a region for limiting movement of the robot as a "virtual safety barrier", defining at least two three-dimensional regions each including a part of the robot including a workpiece and a tool, comparing predicted positions of the three-dimensional regions on a calculated path with the virtual safety barrier, and performing control so as to stop the robot if any of the predicted positions contact the virtual safety barrier.

By using this technique, the movement range of a robot can be limited without depending on a safety barrier or the like, or a safety barrier may be disposed so as to encircle a smaller region. Therefore, the limited floor space of a factory or the like can be efficiently used.

The present invention, which has been achieved in view of such problems, prevents a robot from entering a movement-forbidden region in any circumstances by immediately stopping the robot or raising an alarm so that an operation program is corrected, when it is possible that each axis will enter the movement-forbidden region after coasting in the case that the robot is urgently stopped. An object of the present invention is to provide a method and an apparatus for limiting movement of a robot and a robot system including the apparatus with which floor space and the space of a factory or the like are efficiently used without wasting space by using the function described above.

SUMMARY OF THE INVENTION

According to an aspect of the present invention, a robot system includes a robot and a robot controller that controls the robot, the robot controller including a drive unit that moves the robot, a memory that stores an arm-occupied region and a movement-forbidden region, the arm-occupied region being defined on the basis of an arm of the robot, a tool attached to a wrist of the robot, or a workpiece that is held, the movement-forbidden region being a region that the arm-occupied region is not permitted to enter, a target position calculation unit that calculates a movement target position of the tool or the workpiece for each calculation period and generates a movement command for each axis of the robot, a movement-forbidden region entry monitoring unit that checks whether the arm-occupied region enters the movement-forbidden region, the arm-occupied region being based on the movement target position of the tool or the workpiece that has been calculated by the target position calculation unit, and outputs a stop request to stop movement of the robot if it is checked that the arm-occupied region enters the movement-forbidden region, and a predicted-coasting-position calculating unit that calculates a predicted coasting position of each axis of the robot and a coasting position of the tool or the workpiece when each axis is at the predicted coasting position by estimating a coasting angle of each axis of the robot in a case that the robot is urgently stopped when the robot is moving to the movement target position of the tool or the workpiece and by adding the estimated coasting angle of each axis to the movement command for each axis, wherein the movement-forbidden region entry monitoring unit checks whether the arm-occupied region at the coasting position enters the movement-forbidden region, and, if it is checked that the arm-occupied region at the coasting position enters the movement-forbidden region, outputs another stop request to stop movement of the robot and performs stop control to stop movement of the robot on the stop request.

According to another aspect of the present invention, a robot system includes a robot and a robot controller that controls the robot, the robot controller including a drive unit that moves the robot on the basis of a movement command, a target position calculation unit that calculates, for each calculation period, a movement target position of a tool attached to a wrist of the robot or a workpiece that is held and generates the movement command for each axis of the robot, a memory that stores an arm-occupied region and a movement-forbidden region, the arm-occupied region being defined on the basis of an arm of the robot, the tool, or the workpiece, the movement-forbidden region being a region that the arm-occupied region is not permitted to enter, a present position detection unit that detects a present position of a motor by using a position detector included in each axis of the robot, calculates a present position of the robot from the present position of the motor, and stores the present position of the motor and the present position of the robot, a movement-forbidden region entry monitoring unit that checks whether the arm-occupied region enters the movement-forbidden region, the arm-occupied region being based on the movement target position of the tool or the workpiece calculated by the target position calculation unit, and outputs a stop request to stop movement of the robot if it is checked that the arm-occupied region enters the movement-forbidden region, and a predicted-coasting-position calculating unit that calculates a predicted coasting position of each axis of the robot and a coasting position of the tool or the workpiece when each axis is at the predicted coasting position by estimating a coasting angle of each axis of the robot in a case that the robot is urgently stopped when the robot is moving to the movement target position of the tool or the workpiece and by adding the estimated coasting angle of each axis to the movement command for each axis, wherein the movement-forbidden region entry monitoring unit checks whether the arm-occupied region at the coasting position enters the movement-forbidden region, and outputs another stop request to stop movement of the robot if it is checked that the arm-occupied region at the coasting position enters the movement-forbidden region.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
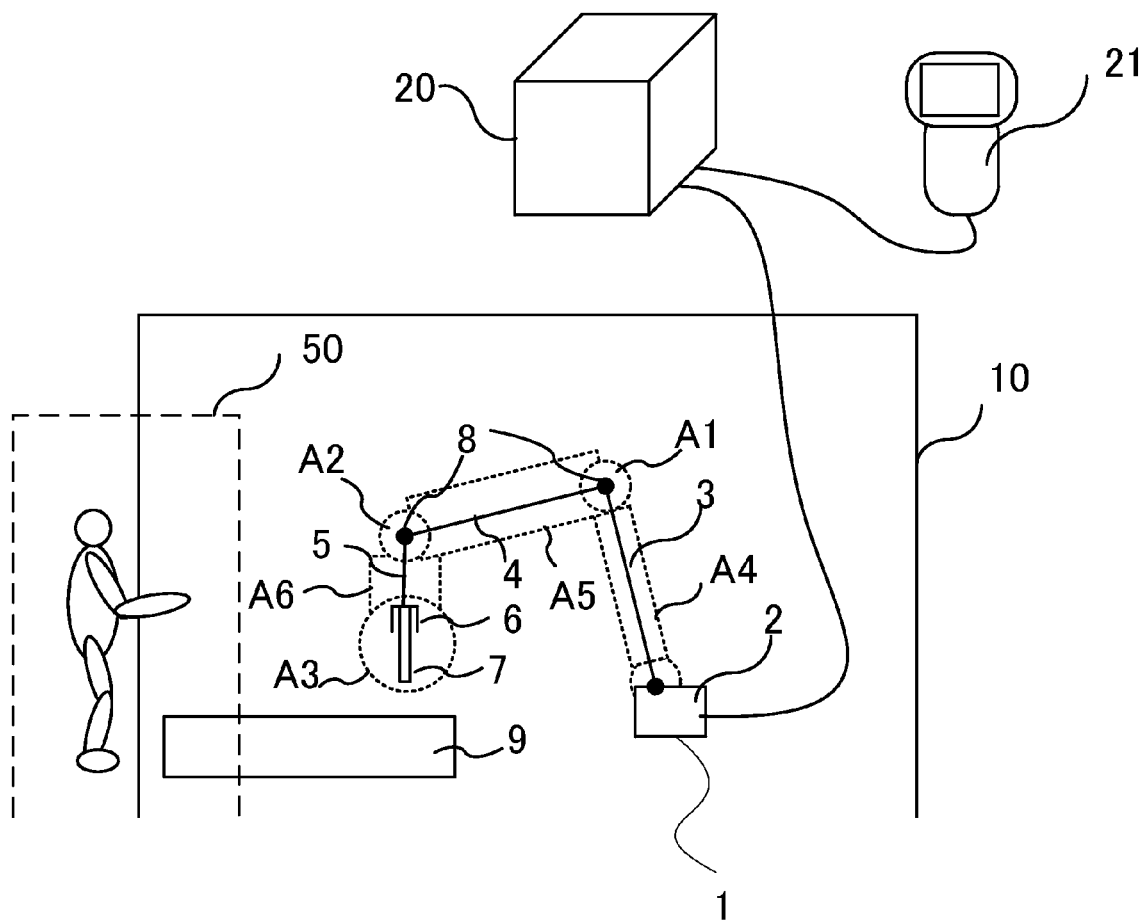
FIG. 1 is a diagram illustrating a method for limiting movement of a robot according to the present invention and a robot system that uses the method.

Embodiments will now be described with reference to the accompanying drawings, wherein like reference numerals designate corresponding or identical elements throughout the various drawings.

First Embodiment

FIG. 1 is a diagram illustrating a method for limiting movement of a robot and a robot system that uses the method according to the present invention. A physical safety barrier 10 is disposed on a floor of a factory, and a robot 1 is disposed in the physical safety barrier 10.

In this example, the robot 1 includes a body 2 and three arms 3, 4, and 5. A tool 7 is attached to the arm 5 with a holding mechanism 6 therebetween. Examples of the tool 7 include a welding torch used for arc welding, a welding gun used for spot welding, and a hand for transporting an object. The arms 3, 4, and 5 are connected to each other through joints 8.

A workpiece 9 is placed on the floor. Examples of the workpiece 9 include an object to be welded and an object to be transported.

A controller 20 sends a necessary signal to the body 2. The arms 3, 4, and 5 move in a predetermined manner in accordance with a predetermined operation program. The holding mechanism 6 or the tool 7 moves along a desired path.

A teach pendant 21 is connected to the controller 20. Teaching of the robot 1, rewriting of an operation program, and the like are performed using the teach pendant 21.

After the robot has been installed and set and before the robot is operated, a movement-forbidden region 50 for the robot 1 is set. In addition to when the robot is installed, the movement-forbidden region 50 is set any time when it is necessary to change the movement-forbidden region 50. The movement-forbidden region 50 is defined by inputting the coordinates of the vertices of the rectangular parallelepiped by using the teach pendant 21, or by moving the control points of the robot 1 by using the teach pendant 21 so as to specify vertices of the rectangular parallelepiped. After the movement-forbidden region 50 has been defined, the movement-forbidden region 50 is stored in a memory of the controller 20. The movement-forbidden region 50 can be defined as a plurality of regions.

Spatial regions occupied by the arms 3, 4, and 5 of the robot 1 and the tool 7 are defined as arm-occupied regions A1, A2, A3, A4, A5, and A6.

The arms 3, 4, and 5 are respectively defined as cylindrical regions A4, A5, and A6 each having a predetermined radius and an axis that is a straight line connecting the joints 8 to each other.

The regions A1 and A2, each including a corresponding one of the joints 8, are each defined as a sphere having a predetermined radius and a center at a point on the axis of the joint 8 of the robot 1. As the point on the axis of one of the joints 8, the intersection of "a straight line connecting the joints 8 to each other", which is used when defining the regions A4, A5, and A6, and the axis of the one of the joints 8 is usually used. The region A3, which includes the holding mechanism 6 and the tool 7 attached to the distal end of the arm 5, is defined as a sphere having a predetermined radius. These definitions of the arm-occupied regions A1 to A6 are stored in the memory of the controller 20.

Figure 2:
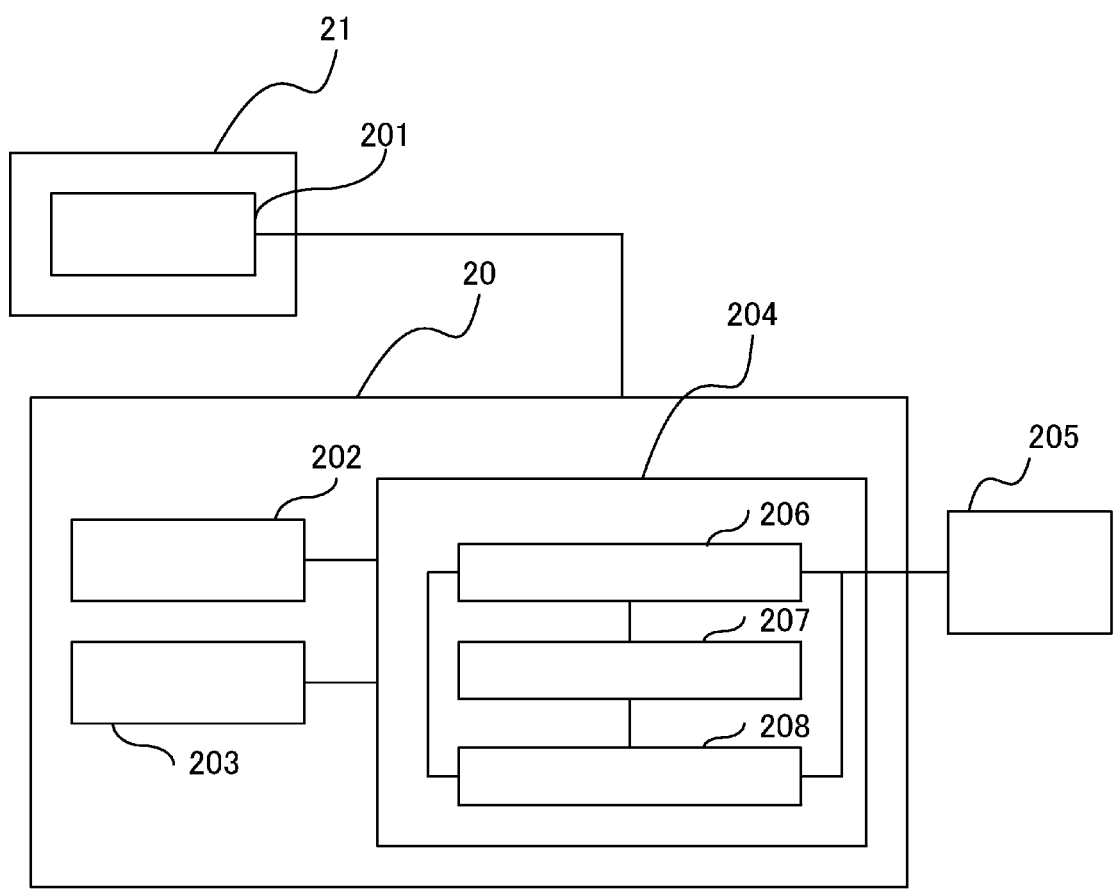
FIG. 2 is a block diagram of the method for limiting movement of a robot according to the present invention.

FIG. 2 is a block diagram illustrating an embodiment of a method for controlling a robot, which is implemented in the controller 20.

In accordance with an operation by an operator on the teach pendant 21, a teach/operation unit 201 calls and executes an operation program and performs a robot operation for teaching the robot. The teach/operation unit 201 also performs storing of taught data (the operation program and other information related to the operation) in a taught data storing area 202 and performs storing of various parameters in a parameter storing area 203. The parameter storing area 203 also stores the dimensions of parts of the arm, which are necessary for interpolation; specifications of the axes, such as the reduction ratios and motor constants, which are necessary for moving the axes of the robot; the radii of the arm-occupied regions A1 to A6; and coordinates and the like for defining the movement-forbidden region 50.

When an operator calls and executes the operation program or performs a robot operation for teaching the robot, the teach/operation unit 201 sends a robot movement request command to a movement command generating unit 204. When the movement command generating unit 204 receives the robot movement request command, a next target position calculation unit 206 calculates an interpolation point on a movement path of a robot as a next target position for each predetermined interpolation period, the movement path having been defined in the operation program. A movement-forbidden region entry monitoring unit 208 checks whether the next target position enters a movement-forbidden region. A predicted-coasting-position calculating unit 207 calculates a position (predicted coasting position) at which the robot will stop after coasting if the robot is urgently stopped when the robot is moving toward the next target position. The movement-forbidden region entry monitoring unit 208 checks whether the predicted coasting position enters the movement-forbidden region. The next target position calculation unit 206 sends to a drive unit 205 a command value for each axis of the robot for moving the robot to a calculated position. However, when the movement-forbidden region entry monitoring unit 208 detects entry to the movement-forbidden region, a stop request is sent to the drive unit 205.

The drive unit 205 moves each axis of the robot 1 in accordance with the command value sent from the movement command generating unit 204. When the drive unit 205 receives the stop request, the drive unit 205 stops the robot 1 instead of moving the robot 1.

Figure 3A:
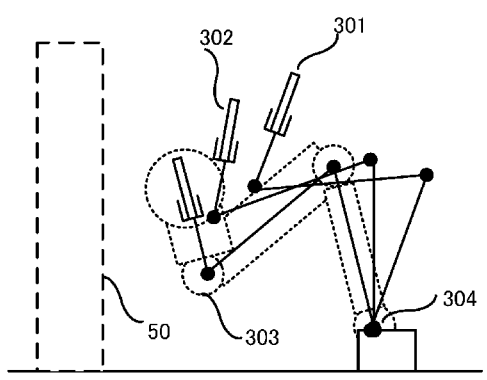
FIGS. 3A and 3B are diagrams illustrating the method for limiting movement of a robot according to the present invention and a robot that uses the method.
Figure 3B:
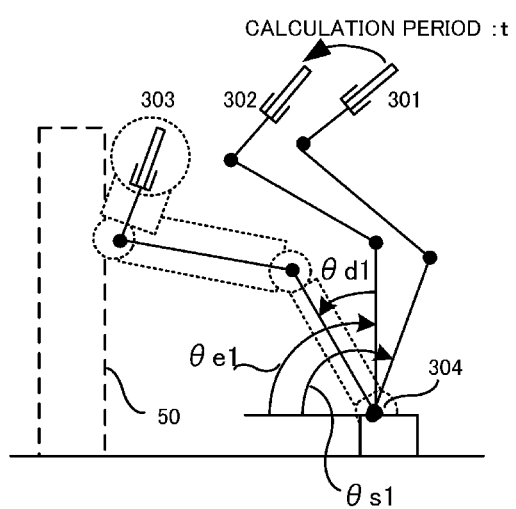

FIGS. 3A and 3B are diagrams illustrating movement of a robot in order to describe fundamental ideas of the present invention.

The robot 1 is moving from a present position 301 to a next target position 302. If the robot 1 is urgently stopped at this moment, each axis coasts to some extent in accordance with the load at the moment and then stops. By predicting the coasting angle of each axis and adding the coasting angle to the next target position, a predicted coasting position 303 can be obtained.

In FIG. 3B, $\theta s1$ is the angle of a first axis 304 at the present position 301, and $\theta e1$ is the angle of the first axis 304 at the next target position 302. $\theta d1$ is the coasting angle when the robot 1 is urgently stopped under the load corresponding to the orientation at the next target position 302. The predicted coasting position 303 can be obtained by calculating $\theta e1 + \theta d1$.

If an arm-occupied region enters the movement-forbidden region 50 when the robot 1 is at the predicted coasting position 303, the robot 1 is stopped before the robot 1 is moved to the next target position 302, so that the robot 1 is prevented from entering the movement-forbidden region 50 after coasting.

The moment of inertia and the gravitational moment for the first axis 304 in the case of FIG. 3B are larger than those in the case of FIG. 3A. Therefore, the coasting angle is larger in the case of FIG. 3B, so that it can be predicted that the arm-occupied region of a wrist enters the movement-forbidden region 50 as illustrated in the figure. Thus, the robot 1 is stopped in the case of FIG. 3B.

Figure 4:
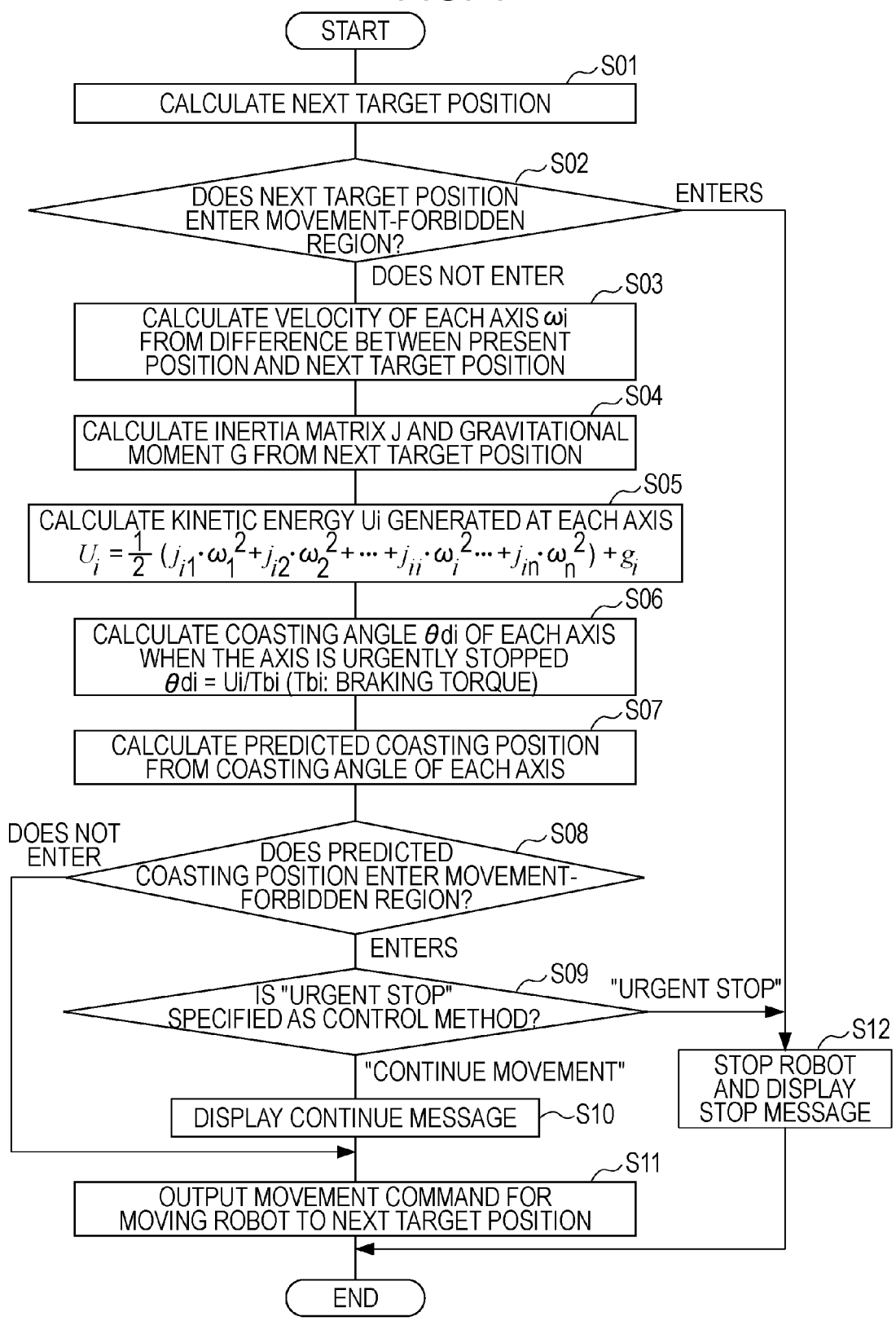
FIG. 4 is a flowchart of the method for limiting movement of a robot according to the present invention.

FIG. 4 is a flowchart of a method implemented in the movement command generating unit 204 for limiting movement of a robot so that the robot does not interfere with the movement-forbidden region. Referring to this figure, the method according to the present invention will be described step by step.

In this description, it is assumed that the robot has n axes. Basically, each step will be repeated for the first axis to n-th axis. The number of each axis will be denoted by the index i. (For example, i=1 . . . 6 for a six-axis robot.)

In step S01, the next target position calculation unit 206 calculates the next target position (302 in FIGS. 3A and 3B) for each calculation period. The next target position includes the angle of each axis of the robot. Next, the process proceeds to step S02.

In step S02, it is checked whether any of the arm-occupied regions A1 to A6 enter the movement-forbidden region 50 when the robot is at the next target position, which has been calculated in step S01. The movement-forbidden region entry monitoring unit 208 performs this check.

There are various methods of entry monitoring. The method used here includes defining the movement-forbidden region as a rectangular parallelepiped, representing the rectangular parallelepiped as six circumscribed spheres each passing through four vertices of a corresponding surface, calculating the distances between the centers of the circumscribed spheres and parts of the arms, and determining whether there exists an interference state using the radii that have been set for the arms and the radii of the circumscribed spheres.

When the movement-forbidden region 50 is defined by a plurality of regions, similar checks are performed for all movement-forbidden regions. If an arm-occupied region enters any of the movement-forbidden regions, it is determined that the arm-occupied region "enters" the movement-forbidden region.

If the determination is "enters", the process proceeds to step S12. Otherwise, the process proceeds to step S03.

In step S03, the velocity $\omega i$ of each axis of the robot is calculated from the difference between the present position and the next target position and from the calculation period t.

The predicted-coasting-position calculating unit 207 calculates the velocity.

For example, the velocity $\omega 1$ of the first axis in FIG. 3B is calculated using the following equation:

$$\omega 1 = (\theta e1 - \theta s1)/t,$$

where $\theta s1$ is the angle of the first axis at the present position, and $\theta e1$ is the angle of the first axis at the next target position as described above.

Likewise, the velocity $\omega i$ is calculated for each of other axes (second to n-th axes). That is, $$\omega i = (\theta ei - \theta si)/t (i=1 \ldots n).$$

Next, the process proceeds to step S04.

In step S04, the predicted-coasting-position calculating unit 207 calculates the inertia matrix J and the gravitational moment G that are generated around each axis of the robot at the next target position.

For the robot having n axes, the inertia matrix J is represented by an n×n matrix, and the gravitational moment G is represented by an n×1 matrix.

$$J = \begin{bmatrix} j_{11} & j_{12} & \cdots & \cdots & j_{1n} \\ j_{21} & j_{22} & & & j_{2n} \\ \vdots & & \ddots & & \vdots \\ \vdots & & & \ddots & \vdots \\ j_{n1} & j_{n2} & \cdots & \cdots & j_{nn} \end{bmatrix}$$

$$G = \begin{bmatrix} g_1 \\ g_2 \\ \vdots \\ \vdots \\ g_n \end{bmatrix}$$

The inertia matrix and the gravitational moment of each axis of the robot can be calculated from the mass, the center of gravity, the shape moment of parts of the arms, which are divided by the joints, and from the angle of each axis of the robot. The mass, the center of gravity, and the shape moment of each part of the arms are stored beforehand in the parameter storing area 203.

The inertia matrix and the gravitational moment of each axis can be calculated from the orientation of the robot by using any of various equations of motion. For example, well-known methods using the "Newton-Euler equation of motion" and "Lagrange equation of motion" are appropriate for real-time computing performed by a computer. Next, the process proceeds to step S05.

In step S05, the predicted-coasting-position calculating unit 207 calculates the energy Ui generated at each axis from the velocity ωi, the inertia matrix J, and the gravitational moment G of each axis, which have been calculated in the steps up to and including step S04.

The total energy acting on a rotating body is represented by the following equation:

$$U = K + P,$$

where U is the total energy, K is the kinetic energy, and P is the potential energy.

In most cases, a robot arm is a rotating body that rotates around each axis. The kinetic energy K of a rotating body is represented by the following equation.

$$K = \frac{1}{2} J \omega^2$$

The potential energy P is equal to the gravitational moment G.

Therefore, the energy Ui of the i-th axis can be calculated using the following equation.

$$U_i = \frac{1}{2}(j_{i1} \cdot \omega_1^2 + j_{i2} \cdot \omega_2^2 + \ldots + j_{ii} \cdot \omega_i^2 \ldots + j_{in} \cdot \omega_n^2) + g_i$$

The energy of each axis is calculated by performing calculation using the above equation for i=1 ... n. Next, the process proceeds to step S06.

In step S06, the predicted-coasting-position calculating unit 207 calculates the coasting angle of each axis when the robot 1 is urgently stopped. The relationship among the energy generated at the i-th axis, the braking capability of the i-th axis, and the coasting angle of the axis is represented by the following equation:

$$Ui = Tbi \cdot \theta di,$$

where Tbi is the braking torque of the i-th axis and θdi is the coasting angle of the i-th axis.

The braking torque Tbi is a characteristic of each axis that is determined by the capability of the mechanical brake of the servo motor, the dynamic brake of the servo amplifier, the regenerative braking, the friction drag of the reduction mechanism, and the like. The larger the braking torque, the smaller the coasting angle of each axis.

Therefore, the coasting angle of the i-th axis when a robot axis that is moving with a certain energy is urgently stopped can be calculated using the following equation.

$$\theta_{di} = U_i / Tb_i$$

The coasting angle θdi of each axis is calculated using this equation. For example, θd1 in FIG. 3B represents the coasting angle of the first axis.

The set value of the braking torque of each axis has been stored in the parameter storing area 203 by using the teach pendant 21 or the like. Next, the process proceeds to step S07.

In step S07, a "predicted coasting position" is calculated on the basis of the coasting angle of each axis, which has been calculated in step S06. The predicted coasting position calculated here is a position that the robot 1 will reach if the robot 1 is urgently stopped at the next target position. For example, in FIG. 3B, the angle of the first axis at the predicted coasting position 303 is the sum of the angle θe1 of the first axis at the next target position 302 and the coasting angle θd1, which has been calculated in step S06. Next, the process proceeds to step S08.

In step S08, it is checked whether the predicted coasting position 303 enters the movement-forbidden region. The method of checking is the same as that of step S02. The movement-forbidden region entry monitoring unit 208 performs this check.

If the determination is "enters", the process proceeds to step S09. Otherwise, the process proceeds to step S11.

In step S09, the process branches to stop control and continuous control in accordance with the control method that an operator has set as a parameter. If the control method is stop control, the process proceeds to step S12. If the control method is continuous control, the process proceeds to step S10.

In step S10, a message "continue movement" or a message having the same meaning and the step number of the operation program at which the predicted coasting position enters the movement-forbidden region in step S08 are displayed on the display of the teach pendant 21. Then, the process proceeds to step S11.

In step S11, a movement command for moving the robot 1 to the next target position, which has been calculated by the next target position calculation unit 206, is output to the drive unit 205, and the robot 1 is moved.

If the process proceeds to step S12, the movement-forbidden region entry monitoring unit 208 sends a stop request to the drive unit 205. Upon receiving the stop request, the drive unit 205 stops movement of the robot 1. A message explaining the reason for stopping is displayed on the display of the teach pendant 21.

With these steps, even when the robot 1 is urgently stopped and the robot 1 coasts, the robot 1 does not enter the movement-forbidden region.

Because the predicted coasting position is off the path that has been actually taught, it is difficult to predict, during teaching operation, whether an interference will occur if the robot 1 coasts.

In the first embodiment, a control method can be selected from "urgent stop" and "continue movement" when it is predicted that the coasting position will enter the movement-forbidden region (step S09).

By utilizing this selection, when checking movement of the robot 1 after the operation program has been taught, the operation program is played back while selecting the "continue movement". By doing so, which parts of the robot 1 may enter the movement-forbidden region if the robot 1 is urgently stopped can be checked, and the teach points and the command velocity can be changed so that interference may not occur during a normal movement. With this function, the possibility of interference during coasting, which is difficult to predict, can be minimized.

This selection can be utilized so as to select "urgent stop" during actual production so that the robot 1 can be urgently stopped if the possibility of interference arises in an abnormal situation.

When setting the movement-forbidden region, it is often easier to define a region in which the robot is allowed to move, i.e., a "movement-allowed region" than to define a region that the robot is not allowed to enter. That is, a region surrounded by a safety barrier is defined.

In such a case, a similar effect is produced by defining a plurality of movement-forbidden regions that surround the movement-allowed region that has been defined.

Figure 5:
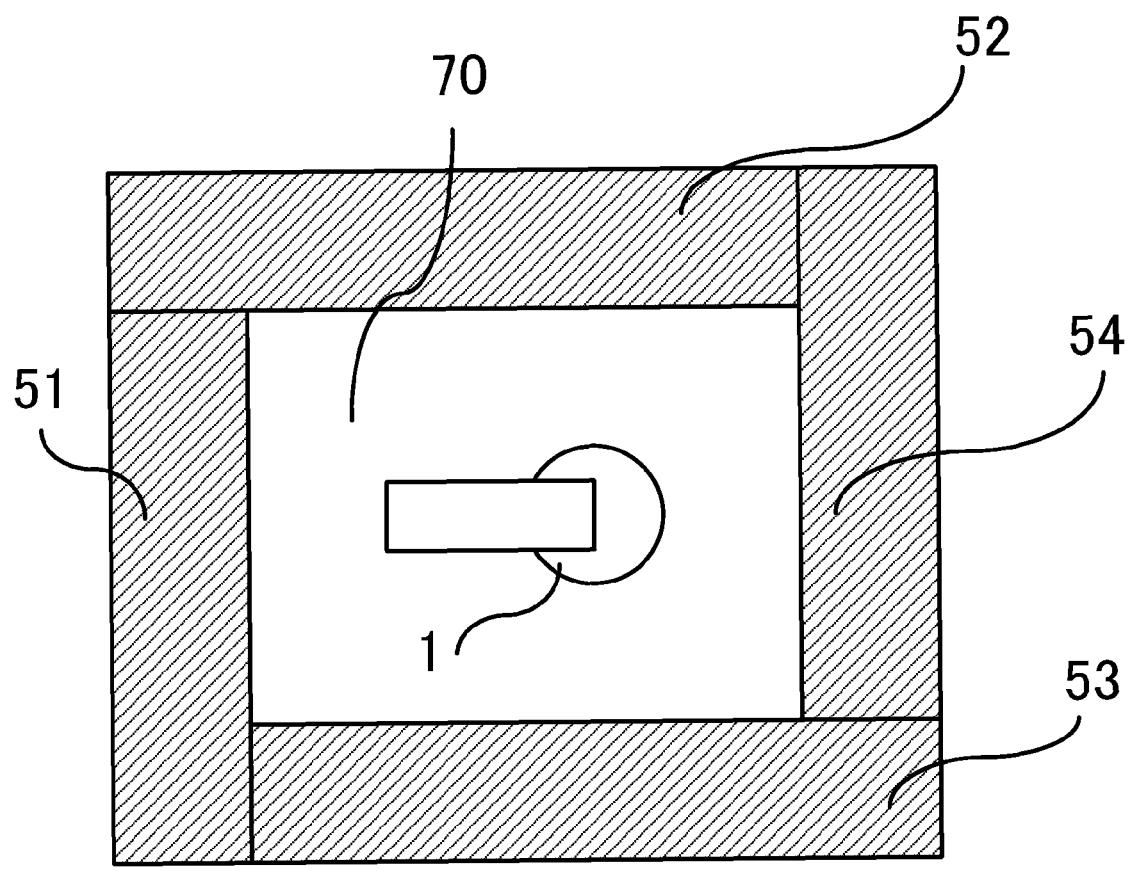
FIG. 5 is a diagram illustrating a method for defining a movement-forbidden region by using a movement-allowed region.

FIG. 5 is a top view of a system in which a movement-allowed region 70 is defined as a rectangular parallelepiped that contains the robot 1.

When a user defines the movement-allowed region 70, the controller automatically generates a plurality of movement-forbidden regions 51 to 54 that are adjacent to the surfaces of the movement-allowed region 70, and stores the movement-forbidden regions 51 to 54 in the parameter storing area 203 beforehand. Thus, motion control that does not allow the robot to move outside the movement-allowed region 70 can be realized by using the method described above.

Second Embodiment

The method of limiting movement of a robot described above is implemented in a control program for controlling a robot. Alternatively, in order to increase safety and reliability, a control apparatus may be independently provided so that the control apparatus monitors whether a robot enters a movement-forbidden region and stops movement of the robot if the robot will enter the movement-forbidden region.

Figure 6:
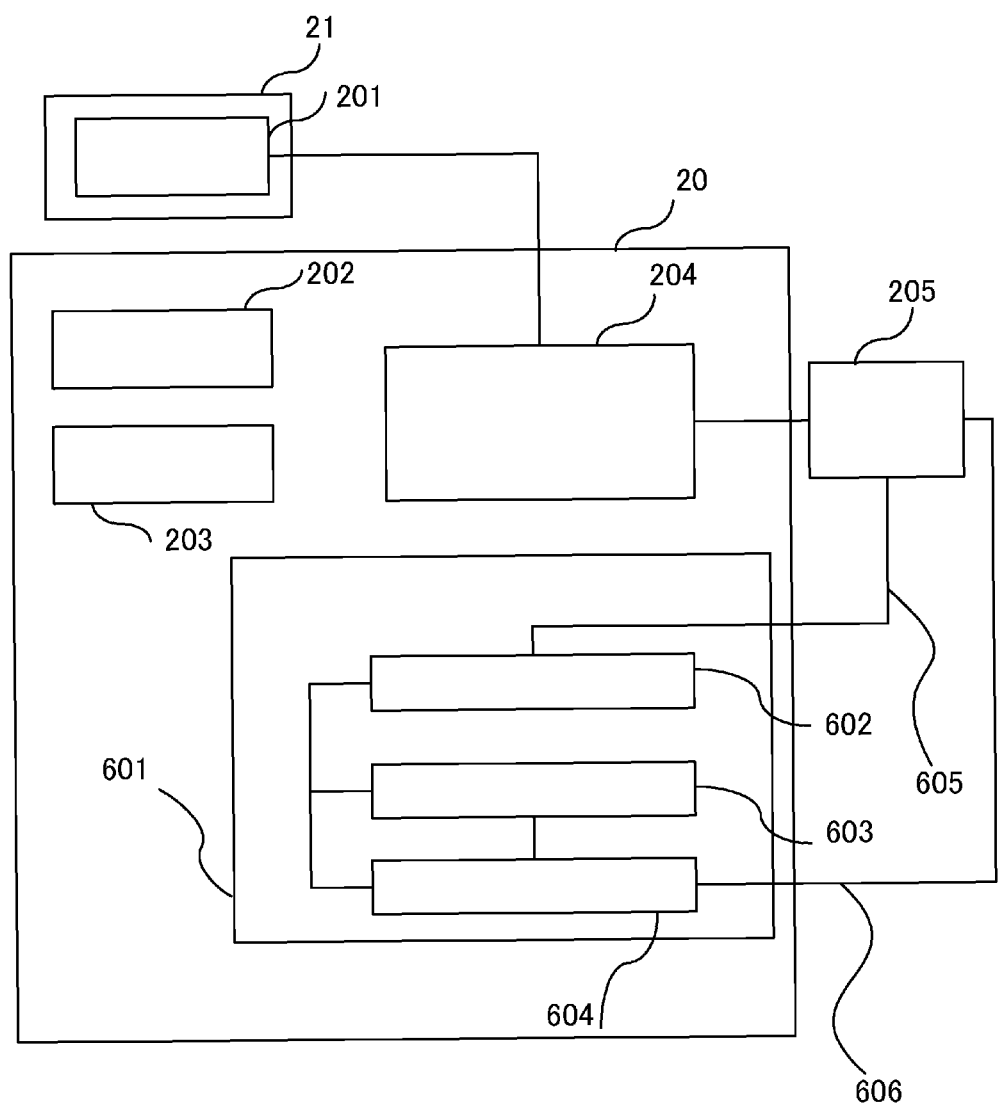
FIG. 6 is a block diagram of a second method for limiting movement of the robot according to the present invention.
Figure 7:
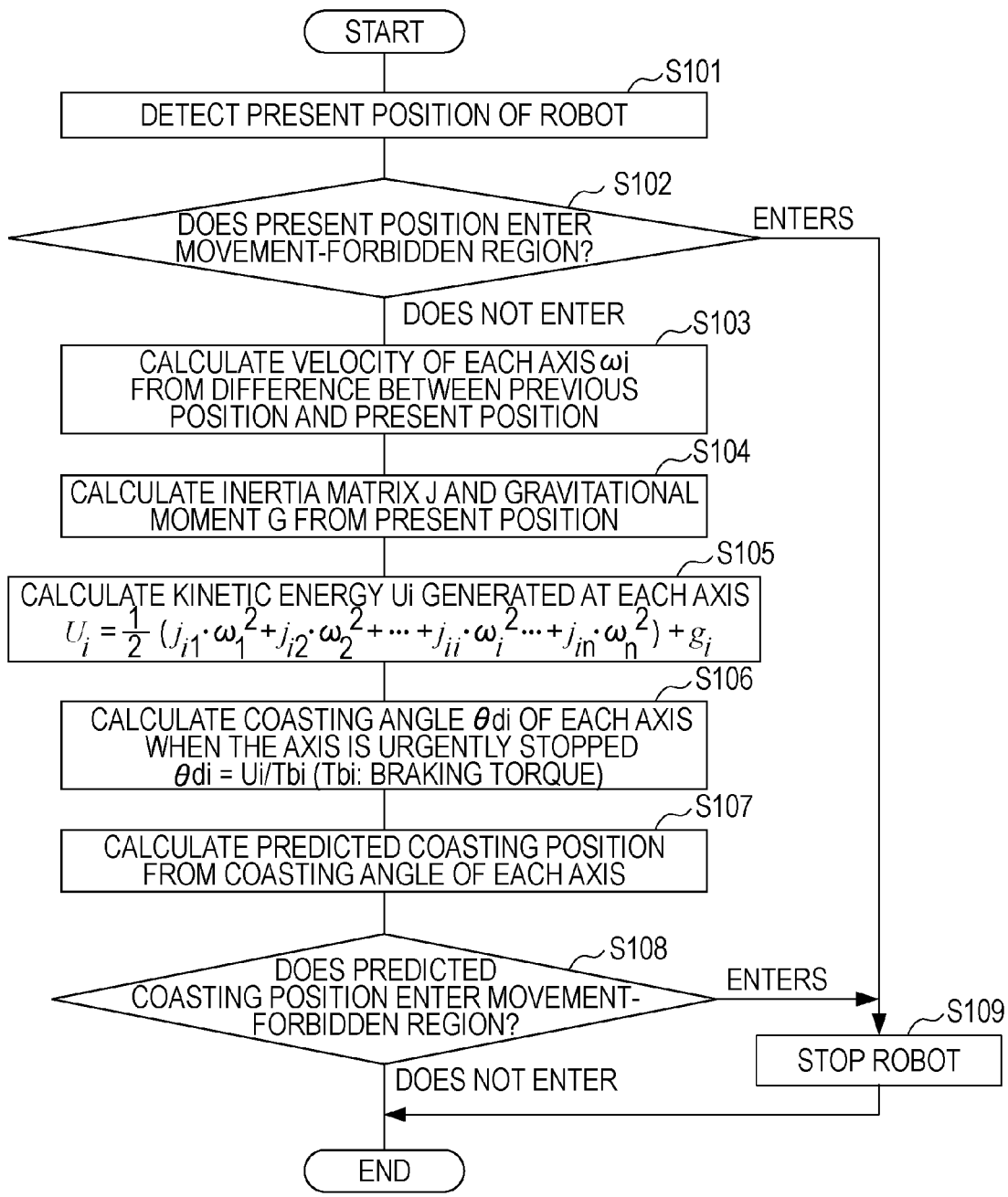
FIG. 7 is a flowchart of the second method for limiting movement of a robot according to the present invention.

FIGS. 6 and 7 illustrate another embodiment of the present invention, which is an independent apparatus that performs such monitoring and stop control.

FIG. 6 illustrates a system in which a movement region monitoring device 601 is added to the system illustrated in FIG. 2. In the movement region monitoring device 601, a present position detection unit 602 reads a motor position 605 of each axis, which is detected by a position detector such as an encoder, from the drive unit 205 for each predetermined monitoring period. From the motor position 605 of each axis, the present position of the robot (the position of a workpiece or a tool, also referred to as TCP) is calculated. A movement-forbidden region entry monitoring unit 604 checks whether the present position of the robot enters the movement-forbidden region. On the basis of the information about the motor position 605 detected by the present position detection unit 602, a predicted-coasting-position calculating unit 603 calculates the position at which the robot will stop after coasting if the robot is urgently stopped at this moment. The movement-forbidden region entry monitoring unit 604 checks whether the predicted coasting position enters the movement-forbidden region. If the movement-forbidden region entry monitoring unit 604 detects that the robot enters the movement-forbidden region, the movement-forbidden region entry monitoring unit 604 outputs an urgent stop request 606, such as a power off signal, to the drive unit 205.

FIG. 7 is a flowchart for limiting movement of a robot using the system illustrated in FIG. 6 so that the robot does not interfere with the movement-forbidden region. By using this figure, a method according to the present invention will be described step by step.

In step S101, the present position detection unit 602 detects the motor position 605 of each axis of the robot. Next, the present position of the robot is calculated from the motor position 605 of each axis that has been detected. For subsequent processing, the present position of the motor of each axis (present position) and the previous position that has been previously detected (previous position) are stored. Next, the process proceeds to step S102.

In step S102, the movement-forbidden region entry monitoring unit 604 checks whether any of the arm-occupied regions A1 to A6 enter the movement-forbidden region 50 when the robot is at the present position that has been calculated in step S101. As a specific method of entry monitoring, a method the same as that used in step S02 of the flowchart of FIG. 4 can be used.

If the determination is "enters", the process proceeds to step S109. Otherwise, the process proceeds to step S103.

In step S103, the velocity ωi of the each axis of the robot is calculated from the difference between the previous position and the present position of the motor of each axis and from the monitoring period. The index i denotes the number of axis. Next, the process proceeds to step S104.

In step S104, the inertia matrix J and the gravitational moment G that are generated around each axis of the robot at the present position of the motor of each axis are calculated. The predicted-coasting-position calculating unit 603 performs these calculations. The method is the same as that of step S04 in FIG. 4. Next, the process proceeds to step S105.

In step S105, the energy Ui generated at each axis is calculated from the velocity ωi, the inertia matrix J, and the gravitational moment vector G of each axis, which have been calculated in the steps up to and including step S104. The predicted-coasting-position calculating unit 603 performs these calculations. The calculation method is the same as that of step S05 in FIG. 4. Next, the process proceeds to step S106.

In step S106, the coasting angle of each axis if the robot is urgently stopped when the motor of each axis is at the present position is calculated. The predicted-coasting-position calculating unit 603 performs these calculations. The calculation method is the same as that of step S06 of FIG. 4. Next, the process proceeds to step S107.

In step S107, a "predicted coasting position" is calculated by adding the coasting angle, which has been calculated in step S106, to the present position of the motor of each axis. The predicted-coasting-position calculating unit 603 performs these calculations. The calculation method is the same as that of step S07 in FIG. 4. Next, the process proceeds to step S108.

In step S108, it is checked whether the predicted coasting position enters the movement-forbidden region. The checking method is the same as that of step S102.

If the determination is "enters", the process proceeds to step S109. Otherwise, the monitoring process for the present monitoring period finishes.

In step S109, an urgent stop request is sent to the drive unit 205.

With the structure and the process described above, even if the movement command generating unit malfunctions and an abnormal command is sent to the robot, the robot can be stopped before the coasting position enters the movement-forbidden region.

With the present invention, movement of a robot is predicted so that whether the robot enters a movement-forbidden region, which is a virtual safety barrier, is statically and dynamically monitored. Therefore, the movement region of the robot can be reliably limited. Instead of a sturdy safety barrier, which has been used to prevent an unintentional deviation of a robot from a movement region, the movement region of the robot can be limited with a simple barrier because the reliability is increased, so that preparation for introducing a robot can be simplified.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A robot system comprising:
    a robot and a robot controller that controls the robot,
    the robot controller including
        a drive unit that moves the robot, a memory that stores an arm-occupied region and a movement-forbidden region, the arm-occupied region being defined on the basis of an arm of the robot, a tool attached to a wrist of the robot, or a workpiece that is held, the movement-forbidden region being a region that the arm-occupied region is not permitted to enter, a target position calculation unit that calculates a movement target position of the tool or the workpiece for each calculation period and generates a movement command for each axis of the robot, a movement-forbidden region entry monitoring unit that checks whether the arm-occupied region enters the movement-forbidden region, the arm-occupied region being based on the movement target position of the tool or the workpiece that has been calculated by the target position calculation unit, and outputs a stop request to stop movement of the robot if it is checked that the arm-occupied region enters the movement-forbidden region, and a predicted-coasting-position calculating unit that calculates a predicted coasting position of each axis of the robot and a coasting position of the tool or the workpiece when each axis is at the predicted coasting position by estimating a coasting angle of each axis of the robot in a case that the robot is urgently stopped when the robot is moving to the movement target position of the tool or the workpiece and by adding the estimated coasting angle of each axis to the movement command for each axis, wherein the movement-forbidden region entry monitoring unit checks whether the arm-occupied region at the coasting position enters the movement-forbidden region, and, if it is checked that the arm-occupied region at the coasting position enters the movement-forbidden region, outputs another stop request to stop movement of the robot and performs stop control to stop movement of the robot on the stop request.

2. The robot system according to claim 1, wherein the robot controller is connected to a teach pendant including a display device and displays a message indicating that the robot is stopped when the robot controller performs stop control to stop movement of the robot on the stop request.

3. The robot system according to claim 1, wherein the robot controller is connected to a teach pendant including a display device and, if a predetermined control method is set to continuous control, displays a message indicating that continuous control of the robot is performed without stopping the robot on the stop request.

4. A robot system comprising:
a robot and a robot controller that controls the robot, the robot controller including a drive unit that moves the robot on the basis of a movement command, a target position calculation unit that calculates, for each calculation period, a movement target position of a tool attached to a wrist of the robot or a workpiece that is held and generates the movement command for each axis of the robot, a memory that stores an arm-occupied region and a movement-forbidden region, the arm-occupied region being defined on the basis of an arm of the robot, the tool, or the workpiece, the movement-forbidden region being a region that the arm-occupied region is not permitted to enter, a present position detection unit that detects a present position of a motor by using a position detector included in each axis of the robot, calculates a present position of the robot from the present position of the motor, and stores the present position of the motor and the present position of the robot, a movement-forbidden region entry monitoring unit that checks whether the arm-occupied region enters the movement-forbidden region, the arm-occupied region being based on the movement target position of the tool or the workpiece calculated by the target position calculation unit, and outputs a stop request to stop movement of the robot if it is checked that the arm-occupied region enters the movement-forbidden region, and a predicted-coasting-position calculating unit that calculates a predicted coasting position of each axis of the robot and a coasting position of the tool or the workpiece when each axis is at the predicted coasting position by estimating a coasting angle of each axis of the robot in a case that the robot is urgently stopped when the robot is moving to the movement target position of the tool or the workpiece and by adding the estimated coasting angle of each axis to the movement command for each axis, wherein the movement-forbidden region entry monitoring unit checks whether the arm-occupied region at the coasting position enters the movement-forbidden region, and outputs another stop request to stop movement of the robot if it is checked that the arm-occupied region at the coasting position enters the movement-forbidden region.

5. The robot system according to claim 4, wherein the memory, the present position detection unit, the predicted-coasting-position calculating unit, and the movement-forbidden region entry monitoring unit are independent from the robot controller.

* * * * *